(12) United States Patent
Cheng

(10) Patent No.: US 8,794,012 B2
(45) Date of Patent: Aug. 5, 2014

(54) METHOD AND SYSTEM FOR CONTROLLED RATE FREEZING OF BIOLOGICAL MATERIAL

(75) Inventor: Alan Cheng, Naperville, IL (US)

(73) Assignee: Praxair Technology, Inc., Danbury, CT (US)

(*) Notice: Subject to any disclaimer, the term of this patent is extended or adjusted under 35 U.S.C. 154(b) by 1196 days.

(21) Appl. No.: 12/266,760

(22) Filed: Nov. 7, 2008

(65) Prior Publication Data

US 2009/0133411 A1   May 28, 2009

Related U.S. Application Data

(60) Provisional application No. 60/986,814, filed on Nov. 9, 2007.

(51) Int. Cl.
| | |
|---|---|
| F25D 25/00 | (2006.01) |
| B01D 8/00 | (2006.01) |
| F17C 7/02 | (2006.01) |
| F25D 3/10 | (2006.01) |
| A01N 1/02 | (2006.01) |

(52) U.S. Cl.
CPC .............. *F25D 3/102* (2013.01); *F02D 29/001* (2013.01); *A01N 1/0252* (2013.01)
USPC .............. 62/62; 62/55.5; 62/52.1; 435/307.1; 73/863.01; 73/863.11

(58) Field of Classification Search
CPC ..... A61B 10/0096; G01N 1/22; G01N 1/2258
USPC ........................ 62/52.1, 66, 62–65, 373, 55.5; 73/863.01, 863.11; 435/307.1
See application file for complete search history.

(56) References Cited

U.S. PATENT DOCUMENTS

| | | | | |
|---|---|---|---|---|
| 3,714,793 | A | * | 2/1973 | Eigenbrod .......................... 62/62 |
| 4,030,314 | A | | 6/1977 | Strehler et al. |
| 4,107,937 | A | | 8/1978 | Chmiel |
| 4,117,881 | A | | 10/1978 | Williams et al. |
| 4,171,625 | A | * | 10/1979 | Morgan et al. .................. 62/380 |
| 4,199,022 | A | | 4/1980 | Senkan et al. |
| 4,199,954 | A | | 4/1980 | McGill |
| 4,304,293 | A | | 12/1981 | Scheiwe et al. |
| 4,314,459 | A | | 2/1982 | Rivoire |
| 4,327,799 | A | | 5/1982 | Scheiwe et al. |
| 4,336,691 | A | | 6/1982 | Burstein et al. |

(Continued)

FOREIGN PATENT DOCUMENTS

| | | |
|---|---|---|
| EP | 0848221 A1 | 6/1998 |
| EP | 1087193 A1 | 3/2001 |

(Continued)

*Primary Examiner* — Allen Flanigan
*Assistant Examiner* — Filip Zec
(74) *Attorney, Agent, or Firm* — Robert J. Hampsch

(57) ABSTRACT

A method and system for controlled rate freezing of biological materials is provided. The presently disclosed system and method provides the ability to rapidly cool the biological materials contained in vials or other containers within a cooling unit via forced convective cooling using a laminar and uniform flow of cryogen in proximity to the plurality of vials disposed within the cooling unit. The rapid cooling of the biological materials is achieved by precisely controlling and adjusting the temperature of the cryogen being introduced to the system as a function of time.

10 Claims, 7 Drawing Sheets

(56) References Cited

U.S. PATENT DOCUMENTS

| | | | |
|---|---|---|---|
| 4,397,158 A * | 8/1983 | Brenik et al. | 62/380 |
| 4,441,327 A * | 4/1984 | Klee et al. | 62/50.5 |
| 4,455,842 A | 6/1984 | Granlund | |
| 4,459,825 A | 7/1984 | Crouch | |
| 4,480,682 A | 11/1984 | Kaneta et al. | |
| 4,481,780 A * | 11/1984 | Delano | 62/46.1 |
| 4,531,373 A | 7/1985 | Rubinsky | |
| 4,537,034 A | 8/1985 | Crouch | |
| 4,739,622 A | 4/1988 | Smith | |
| 4,792,302 A * | 12/1988 | Baker et al. | 432/59 |
| 4,969,336 A * | 11/1990 | Knippscheer et al. | 62/266 |
| 5,044,165 A | 9/1991 | Linner et al. | |
| 5,048,300 A * | 9/1991 | Lihl | 62/48.1 |
| 5,073,208 A | 12/1991 | Wong et al. | |
| 5,321,955 A | 6/1994 | Leonard | |
| 5,328,821 A | 7/1994 | Fisher et al. | |
| 5,402,649 A * | 4/1995 | Glasser | 62/54.1 |
| 5,469,711 A * | 11/1995 | McCoy | 62/51.1 |
| 5,493,865 A | 2/1996 | Wohlwend | |
| 5,660,047 A * | 8/1997 | Paganessi | 62/64 |
| 5,897,309 A * | 4/1999 | Katz et al. | 432/77 |
| 5,964,100 A * | 10/1999 | Wisniewski | 62/373 |
| 6,044,648 A | 4/2000 | Rode | |
| 6,267,925 B1 | 7/2001 | Pages | |
| 6,300,130 B1 | 10/2001 | Toner et al. | |
| 6,519,954 B1 | 2/2003 | Prien et al. | |
| 6,615,914 B1 | 9/2003 | Young | |
| 6,635,414 B2 | 10/2003 | Wisniewski | |
| 6,684,646 B2 | 2/2004 | Voute et al. | |
| 6,745,577 B2 * | 6/2004 | Newman | 62/52.1 |
| 6,786,054 B2 | 9/2004 | Voute et al. | |
| 6,945,056 B2 | 9/2005 | Brown et al. | |
| 6,996,995 B2 | 2/2006 | Voute et al. | |
| 7,104,074 B2 | 9/2006 | Voute et al. | |
| 7,137,261 B2 | 11/2006 | Brown et al. | |
| 7,353,658 B2 | 4/2008 | Voute et al. | |
| 2005/0091992 A1 * | 5/2005 | Aggarwal et al. | 62/62 |
| 2007/0012051 A1 * | 1/2007 | Acton et al. | 62/70 |
| 2008/0048047 A1 * | 2/2008 | Zurecki et al. | 239/8 |
| 2009/0133410 A1 * | 5/2009 | Thorne et al. | 62/62 |

FOREIGN PATENT DOCUMENTS

| | | |
|---|---|---|
| EP | 1793185 A2 | 6/2007 |
| WO | WO 01/93675 A1 | 12/2001 |
| WO | WO 01/95716 A2 | 12/2001 |

* cited by examiner

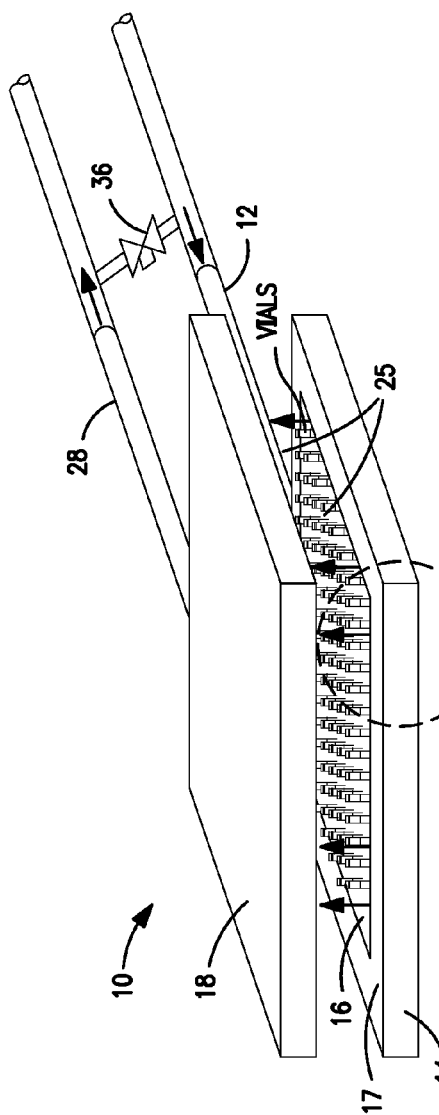
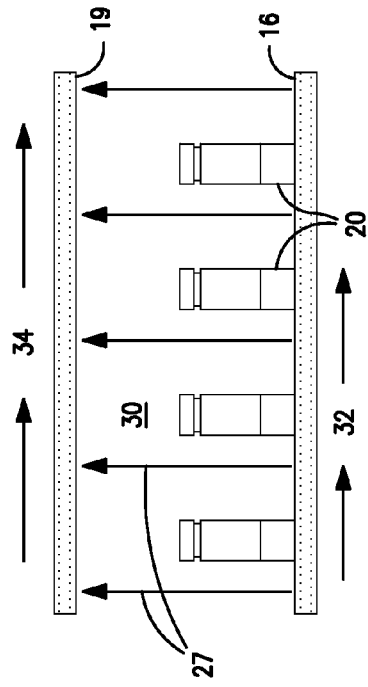
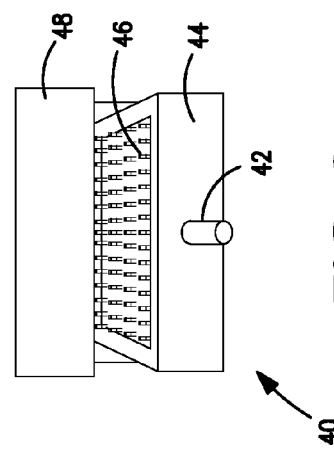

METHOD AND SYSTEM FOR CONTROLLED RATE FREEZING OF BIOLOGICAL MATERIAL

CROSS REFERENCE TO RELATED APPLICATIONS

The present application claims priority from U.S. provisional patent application Ser. No. 60/986,814 filed on Nov. 9, 2007 the disclosure of which is incorporated by reference herein.

FIELD OF THE INVENTION

The present invention broadly relates to a cryopreservation process, and more particularly, to a method and system for providing controlled rate freezing of biological materials that minimize cell damage resulting from intercellular ice formation and solute effects that arise during the cryopreservation process.

BACKGROUND OF THE INVENTION

Cryopreservation is a process used to stabilize biological materials at very low temperatures. Previous attempts to freeze biological materials, such as living cells often results in a significant loss of cell viability and in some cases as much as 80% or more loss of cell activity and viability.

In some cases, cell damage during cryopreservation usually occurs as a result of intracellular ice formation within the living cell during the freezing step or during recrystallization. Rapid cooling often leads to formation of more intracellular ice since water molecules are not fully migrated out of the cell during the short timeframe associated with the rapid cooldown rates. Intercellular ice formation also can arise during recrystallization that occurs during the warming or thawing cycles. If too much water remains inside the living cell, damage due to initial ice crystal formation during the rapid cooling phase and subsequent recrystallization during warming phases can occur and such damage is usually lethal.

On the other hand, slow cooling profiles during cryopreservation often results in an increase in the solute effects where excess water is migrated out of the cells. Excess water migrating out of the cells adversely affects the cells due to an increase in osmotic imbalance. Thus, cell damage occurs as a result of osmotic imbalances which can be detrimental to cell survival and ultimately lead to cell damage and cell viability.

Current cryopreservation techniques involve using either conductive based cryogenic cooling equipment such as a cold shelf or lyophilizer type freezer unit or convective based cryogenic cooling equipment such as controlled rate freezers and cryo-cooler units. Such equipment, however, are only suitable for relatively small volume capacities only and not suitable for commercial scale production and preservation of biological materials such as therapeutic cell lines. For example, the largest commercially available controlled rate freezer suitable for use with biological materials holds only about 8000 or so closely packed vials. Such existing controlled rate freezers also suffer from the non-uniformity in cooling vial to vial due, in part, to the non-uniform flow of cryogen within the freezers and the requirement for close packing of the vials within the freezer.

Many conventional freezing systems utilize internal fans to disperse cryogen around the unit and deliver the refrigeration to the vials via convection. Such convection based cooling or freezing systems cannot achieve temperature uniformity as the vials are often located at various distances from the internal fan or packed in the shadow of other vials or trays. Vials of biological material exposed to high velocity turbulent flow of cryogen are typically cooled at a different rate and often much faster than vials situated further away from the fan.

There are also existing lyophilizer type of control rate freezers that can handle large volume of vials but typically rely on thermal conduction between cold shelves in the lyophilizer unit to the vials. However, it is impossible to make the bottom of glass vials to have uniform conductive surface area since most glass vial bottoms are concave. Therefore, temperature variations during the freezing process from vial to vial are the biggest drawback for these types of equipment. Furthermore, the cooling rate can be painfully slow due to very small conductive surface of the vial that remains in contact with the cold shelves.

Prior attempts to mitigate the loss of cell activity and viability involved the use of cryoprotective additives such as DSMO and glycerol. Use of such cryoprotectives during the cryopreservation process has demonstrated a reduction in cell losses attributable to the freezing and subsequent thawing cycles. However, many cryoprotectants such as DSMO are toxic to human cells and are otherwise not suitable for use in whole cell therapies. Disadvantageously, cryoprotectants also add a degree of complexity and associated cost to the cell production and preservation process. Also, cryoprotectants alone, have not eradicated the problem of loss of cell activity and viability.

What is needed is a method and system to further reduce or minimize cell damage occurring due to ice formation or solute effects during cryopreservation processes with or without the use of cryoprotectives. Moreover, the system and method should be both efficient and readily scaleable to handle commercial scale production and preservation of biological materials and provide rapid and uniform cooling of such biological material.

SUMMARY OF THE INVENTION

The present invention may be characterized as a cryogenic chiller or freezing system for biological materials that includes a cryogen source, an intake circuit coupled to the cryogen source and adapted for providing a uniform flow of a cryogen cold gas to a cooling chamber, an exhaust circuit and a control system. The cooling chamber comprises an intake plenum, an exhaust manifold, and two or more parallel porous surfaces that define a cooling area between adjacent parallel surfaces with one of the parallel porous surfaces disposed adjacent to the intake plenum and in fluid communication with the intake plenum and another of the parallel porous surfaces disposed adjacent to the exhaust manifold, the parallel porous surfaces and cooling area adapted to retain a plurality of containers of biological materials. The exhaust circuit of the freezing or chilling system is adapted to remove the cryogen gas from the exhaust manifold of the cooling chamber whereas the control system is adapted to adjust the flow rates of the cryogen source in the intake circuit and any cryogen gas in the exhaust circuit to adjust the temperature of the cold cryogen gas delivered to the cooling chamber in response to a desired cooling rate of the biological materials and measured temperatures within the cooling chamber. In this manner, a uniform, unidirectional, and laminar flow of temperature adjusted cryogenic cold gas is delivered to the cooling area between the parallel porous surfaces and each of the plurality of containers to uniformly cool the biological materials.

The present invention may be characterized as a method of controlled rate freezing or chilling of biological materials comprising the steps of: (i) placing a plurality of containers of the biological materials in a cooling area defined as the area between parallel porous surfaces within a cooling chamber; (ii) mixing a liquid cryogen with a warmer gas to produce a cold cryogenic gas at a selected temperature profile, the temperature profile corresponding to a desired cooling rate of the biological materials within the containers; (iii) delivering a uni-directional, laminar flow of the temperature adjusted cryogenic cold gas through one of the porous surfaces to the cooling area between the parallel porous surfaces and each of the plurality of containers to uniformly cool the biological materials; and (iv) promptly exhausting the gas from cooling chamber via another parallel porous surface so as to prevent recirculation of the gas within the cooling area.

BRIEF DESCRIPTION OF THE DRAWINGS

The above and other aspects, features, and advantages of the present invention will be more apparent from the following, more detailed description thereof, presented in conjunction with the following drawings, wherein:

FIG. 1 is a schematic illustration of an embodiment of a uniform flow cryogenic chiller unit adapted for use with the present system and method;

FIG. 2 is a detailed view of a cut-away portion the uniform flow cryogenic chiller unit of FIG. 1 depicting the uniform flow characteristics of the cryogen gas proximate the vials of biological materials;

FIG. 3 is a picture of an embodiment of a single batch uniform flow cryogenic chiller unit incorporating the features and advantages of the presently disclosed system and method;

DETAILED DESCRIPTION OF THE INVENTION

Cryopreservation of biological materials typically involves rapid cooling of biological specimens from temperatures of 40° C. or more to temperatures of about −100° C. or lower. The specified temperatures, cool-down rates, and cooling profiles, expressed as temperature of the materials as a function of time, are highly dependent on the specific biological materials to be frozen. In most cryopreservation of biological materials, the freezing process must be precisely controlled. Uniformity in temperatures, cool-down rates, and cooling profiles from vial to vial and batch to batch is of utmost importance in the production process.

The presently disclosed method and system represents an improvement to current cryopreservation processes for biological materials. The presently disclosed system and method provides the ability to rapidly cool the biological materials contained in vials or other containers within a cooling unit primarily via forced convective cooling using a laminar and uniform flow of cryogen in proximity to each of the plurality of vials disposed within the cooling unit. In addition, the present system and method are capable of providing the rapid cooling of the biological materials over a wide range of cooling rates and also hold the temperature of the biological materials at any prescribed temperature where specified.

Figure 6:
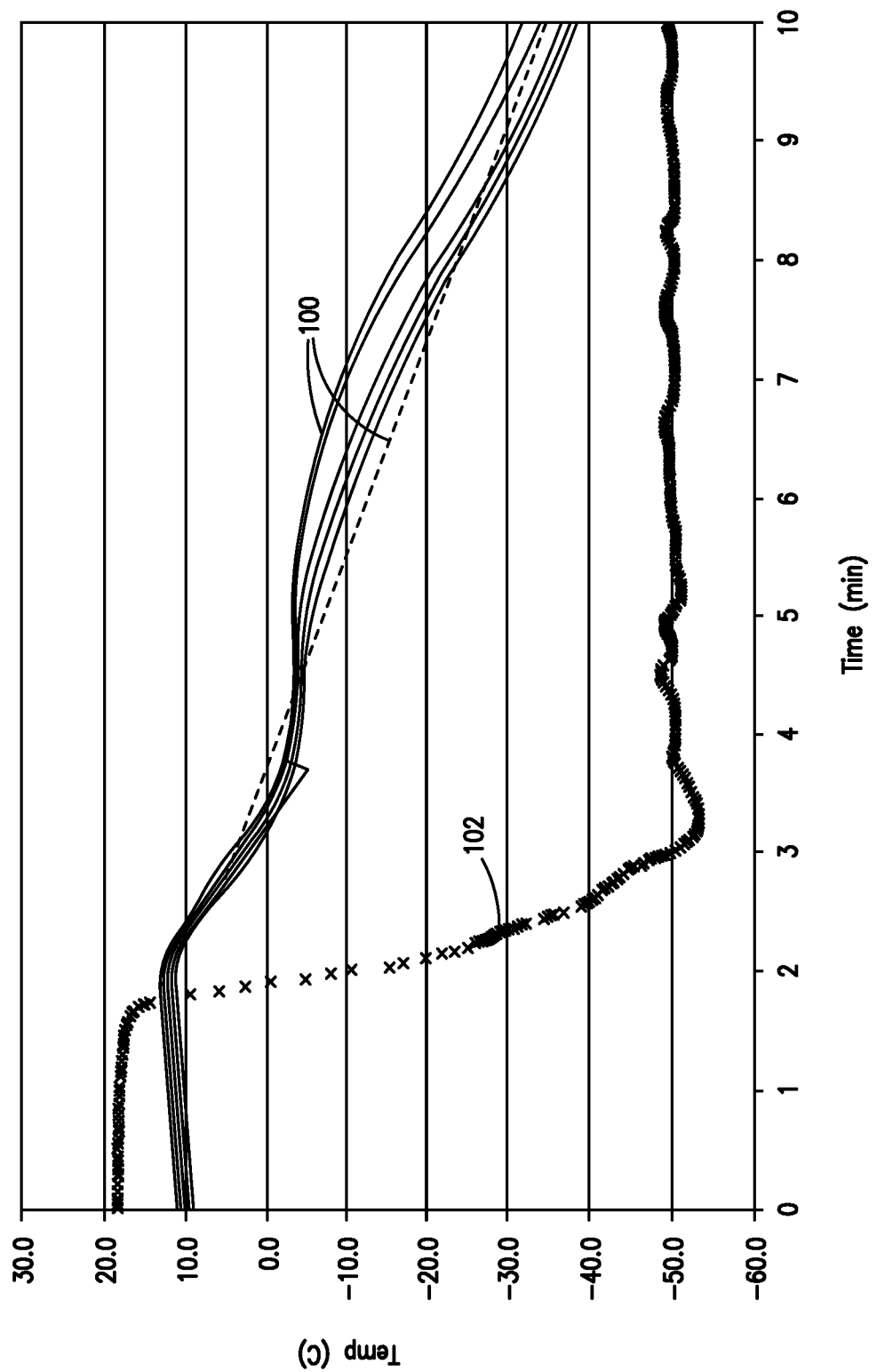
FIGS. 6 through 8 depict selected temperature profiles of the cryogen gas and corresponding relationship to the cooling rates of biological materials observed during initial experiments of the present system and methods.
Figure 7:
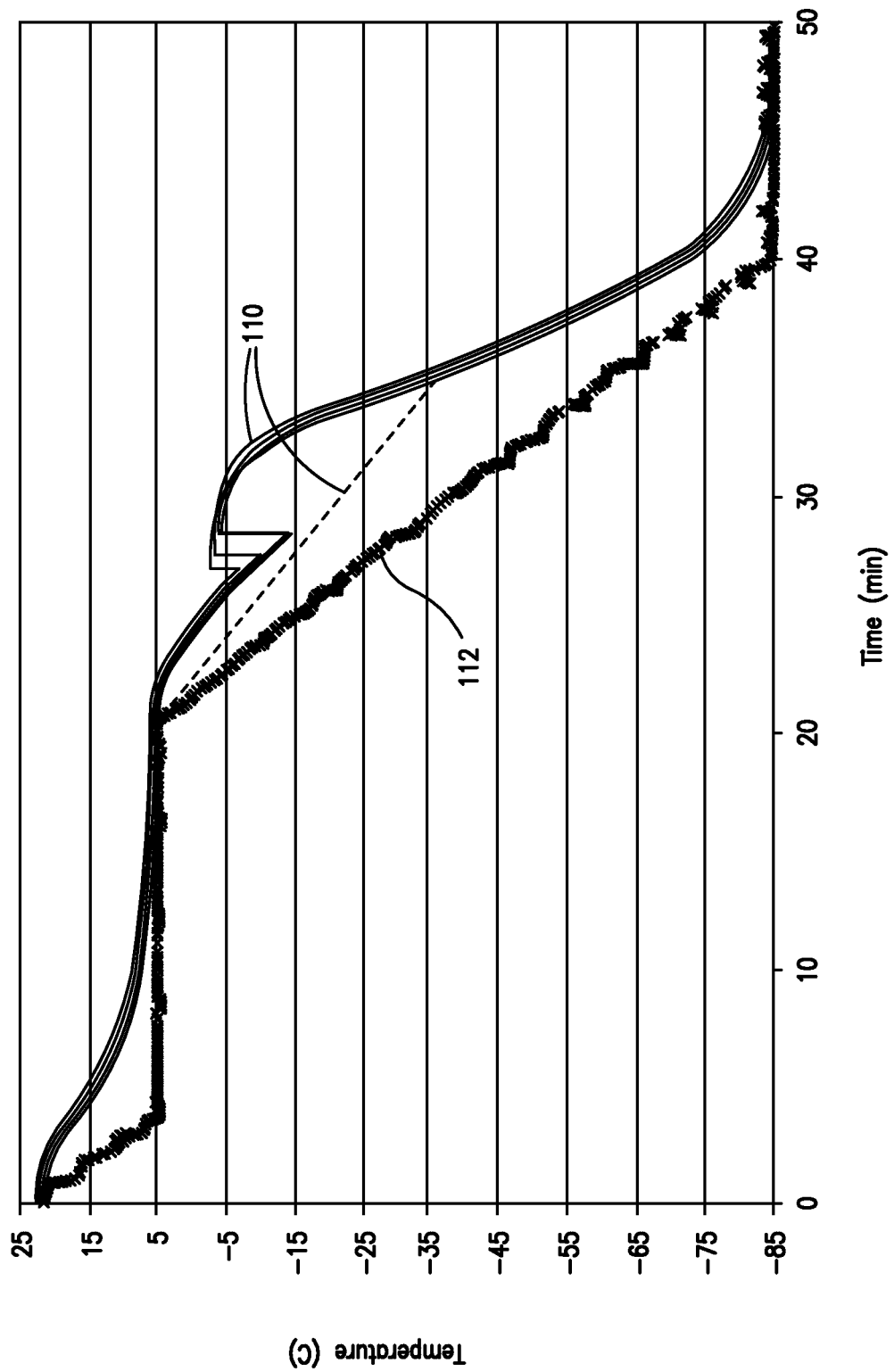
Figure 8:
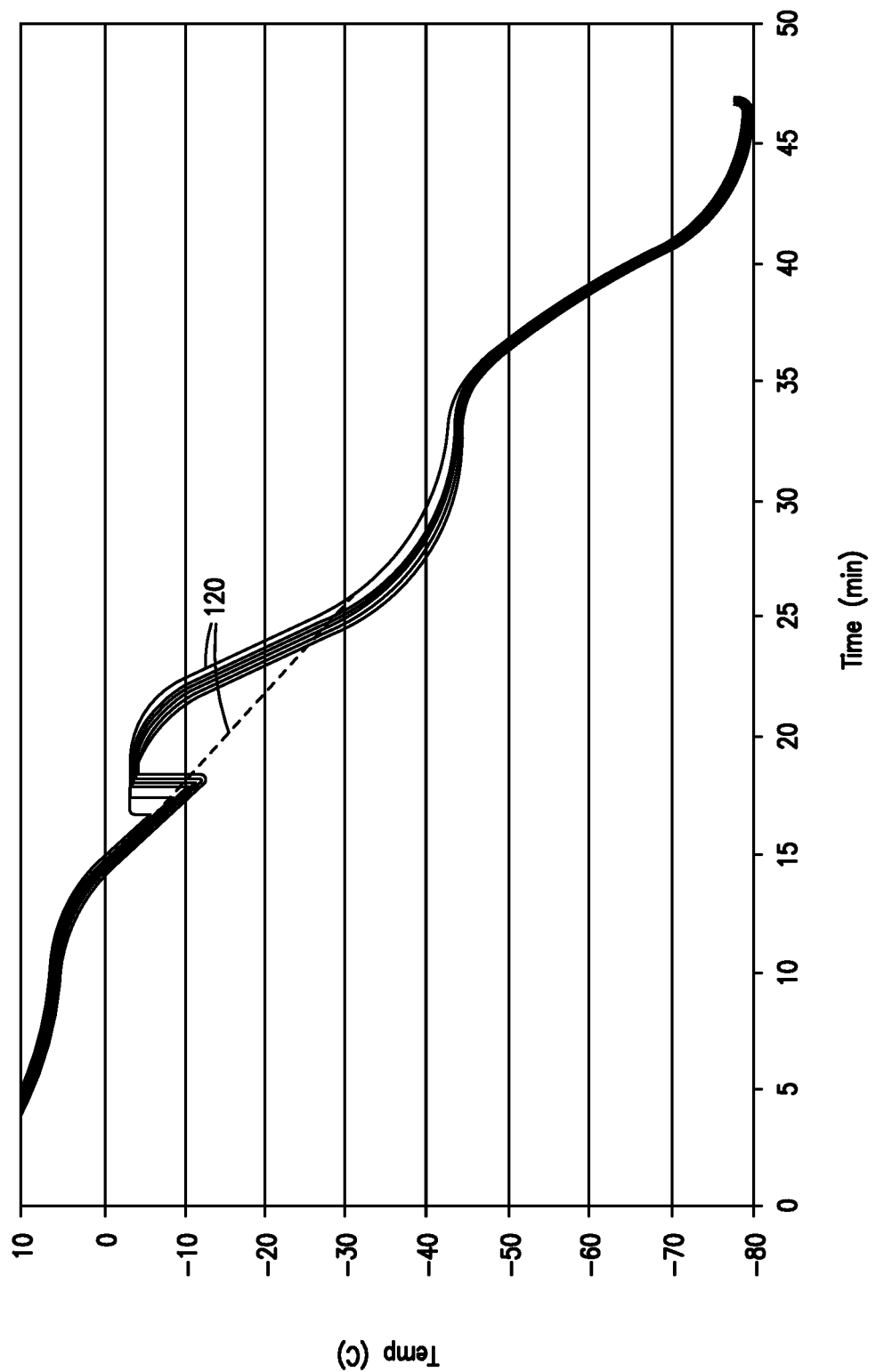

More specifically, the rapid cooling of the biological materials is achieved by precisely controlling and adjusting the temperature of the cryogen being introduced to the system as a function of time. In one mode, the disclosed embodiments of the system are adapted to provide a stepwise or quick drop in cryogen temperature 102 (See FIG. 6) to generate a higher degree of sub-cooling within the sample materials 100 thereby minimizing the exothermic effects of the phase transition (e.g. water-to-ice transformation) in the vials. In another mode, the disclosed embodiments of the present controlled rate freezing or cryogenic chilling system and method are adapted to provide a ramp down of cryogen cold gas temperature of about −4.5° C. per minute 112 (See FIG. 7) and of about −5.0° C. per minute (See FIG. 8) to provide rapid cooling of the sample biological materials 110, 120 yet minimize any vial to vial variations in temperature.

Temperatures of the cold cryogen gas introduced to the cooling chamber or unit are adjusted or controlled by mixing a source of liquid nitrogen with a source of warmer nitrogen gas just prior to introduction of the cold cryogen gas to the cooling unit. The mixed flow is then introduced and dispersed throughout the cooling unit by means of suitable cryogen intake circuits, as described herein. The warmer nitrogen gas is preferably either room temperature nitrogen gas from a supply source or nitrogen gas exiting from the cooling unit and recycled to the cryogen intake circuit. The warmer nitrogen gas mixed with the cold nitrogen liquid or gas also acts as a motive gas and preferably has a volumetric flow rate many times that of the liquid or cold nitrogen. Through the appropriate mixing of the warmer nitrogen gas with the cooler nitrogen flow, the present system creates a laminar and uniform flow of the cryogen across the entire cooling area targeted by the cold cryogen gas. By recycling the nitrogen gas exiting the cooling unit(s), the presently disclosed system and method also offers a higher utilization efficiency of the cryogen (e.g. nitrogen) than existing controlled rate freezers.

Given the uniform flow of the cold cryogen gas across all samples or vials of the biological material, it has been found that precise control of the cold cryogen gas temperature and cryogen temperature gradient has a direct correlation to the observed cooling rates of the biological material within the cooling unit, for a given biological material. For example, when the cold cryogen gas temperature provided to the present cooling unit at is varied or ramped at about −4.5° C./min to about −5.0° C./min, an average cooling rate of the biological material of approximately −2.5° C./min is achieved with minimum vial-to-vial temperature variations. (See FIGS. 7 and 8).

Turning now to FIGS. 1 and 2, there are depicted selected views of a cooling unit, referred to as a uniform flow cryogenic chiller 10. As seen therein, the uniform flow cryogenic chiller 10 includes a cryogen intake circuit 12 or conduit coupled to a source of cryogen (not shown). The uniform flow cryogenic chiller 10 further includes a base gas injection box 14, a porous metal plate 16 disposed or set in or near the top surface 17 of the gas injection box 14, and a corresponding gas removal box 18 positioned immediately above the base gas injection box 14 and a porous metal plate 19 disposed therein. Alternatively, various arrangements of supported polymeric membranes suitable to withstand the cryogenic temperatures or other perforated plates with mechanically punctured or chemically etched holes can be used in lieu of the porous metal plates.

The porous metal plate 16 associated with the gas injection box 14 is adapted to receive and hold a plurality of vials 20 containing biological materials. Also disposed in or near the vials 20 is a plurality of temperature sensors 25 to be used as inputs to the system controller (not shown). The cryogen intake circuit 12 or conduit is further coupled to the gas injection box 14 that is adapted to receive the cryogen intake flow and evenly distribute the cryogen across the porous metal plate 16. The cold cryogen gas flows in a uniform manner into an intake plenum 32 in the gas injection box 14 through the lower porous metal plate 16 holding the vials 20 into the cooling space 30 and then to the gas removal box 18 which also includes an upper porous metal plate 19 and an exhaust manifold 34. From the exhaust manifold 34, the spent nitrogen gas exits via the gas exhaust circuit 28 or conduit.

As discussed above, the cooling of the vials 20 is provided by the heat transfer between the vials 20 and the cryogenic cold gas 27 flowing through the cooling area 30. The cryogenic cold gas 27 is produced in the cryogen intake circuit 12 by mixing liquid nitrogen with a warmer nitrogen gas or recirculating spent nitrogen gas from the gas exhaust circuit 28 with appropriate mixing apparatus or valves 36. The vials 20 are cooled generally at slightly slower rate than the cryogenic cold gas. The temperature difference between the vials 20 and the cryogenic cold gas 27 is the thermal driving force to cool down the vials 20. Therefore, it is possible to freeze the vials 20 with any temperature profile by precisely controlling the temperature of the cryogenic cold gas 27 at a particular temperature profile.

Preferably, the cryogenic cold gas temperature, and more particularly, the temperature profile is actively controlled in response to the average temperatures indicated by the temperature or thermal sensors 25 disposed at or near the vials 20. In the present embodiment, the average temperatures in a plurality of vials 20 are being used as the inputs for the active control of the system. Preferably, a cascade based control methodology where the system temperatures including vial temperatures are monitored and controlled by a primary system controller, which transfers set point signals and other commands to a slave controller responsible for modulating the cryogenic cold gas temperatures in the intake circuit. As discussed in more detail below, the cryogenic cold gas temperature profile is created through the operative control of a mixing valve that blends a specified volume of cold liquid nitrogen with a specified volume the warmer nitrogen gas. The blending or mixing is preferably a continuous operation that changes as a function of time to yield a cryogenic cold gas having a temperature a prescribed temperature profile (i.e. temperature that changes as a function of time). In short, operative temperature control of the uniform flow cryogenic chiller is achieved by controlling the temperature profile of the cryogen cold gas in the intake circuits. As discussed above, it has been found that precise control of the cold cryogenic gas temperatures and temperature gradients has a direct correlation to the observed cooling rates of the given biological material.

As the cryogenic cold gas enters the lower gas injection box 14, the cryogenic cold gas 27 is dispersed into an intake plenum 32 through a series of downward oriented sparger pipes or channels within the gas injection box (not shown). This dispersion in the intake plenum 32 promotes an even distribution of the cryogenic cold gas 27 across the entire surface of the porous metal plate 16 The downward oriented distribution of cryogenic cold gas 27 in the intake plenum 32 avoids the direct impingement of the cryogenic cold gas 27 on the porous metal plate 16, resulting in cold sports and non-uniform cooling. The porous metal plate 16 in the gas injection box 14 forces the cryogenic cold gas 27 to distribute uniformly across the entire cooling area 30 of the uniform flow cryogenic chiller 10, where the vials or other containers of biological material are held. The spent nitrogen is collected in an exhaust manifold 34 disposed above the porous plate 19 in the gas removal box 18. As illustrated, the cold cryogenic gas 27 has only a short path to traverse from the intake plenum 32 through the porous plate 16 upward into the cooling area 30, through the upper porous plate 19 and into the exhaust manifold 34. The uniform direction and short distance of the cryogenic cold gas flow results in a high level of uniformity in vial 20 cooling within the cryogenic chiller 10. Pore sizes for the porous metallic plates 16, 19 are preferably on the order of about 2 to 50 microns in diameter, as small pores enhance the dispersion and resulting uniformity in cooling. By cooling or freezing the biological material at the optimized rate, the survival rate of the cells is enhanced yielding potentially higher drug potency.

At the freezing point of the solutions, the heat of crystallization keeps the solution temperature from dropping, and sometime the temperature within the vial can also rise. Using one or more thermal or temperature sensors 25 embedded in or near selected control vials, the temperature of cryogenic cold gas can be adjusted to minimize temperature deviation from the optimized cooling rate, as needed. In other words, control of the system may be either pre-programmed or may be a real-time feedback based operation.

Pharmaceutical, biopharmaceutical or biologic solutions contained in vials or containers for cryopreservation would benefit from the present system and methods. Such biological or biopharmaceutical materials may include microorganisms, tissues, organs, stem cells, primary cells, established cell lines, small multicellular organisms, complex cellular structures such as embryos, or a solution or mixture that includes: a live or attenuated viruses; nucleic acids; monoclonal antibodies; polyclonal antibodies; biomolecules; nonpeptide analogues; peptides, proteins, including fusion and modified proteins; RNA, DNA and subclasses thereof, oligonucleotides; viral particles; and similar such materials or components thereof. Also, the containers used for holding the biological materials may include vials, straws, polymeric bags, or other form of suitable container.

Figure 4:
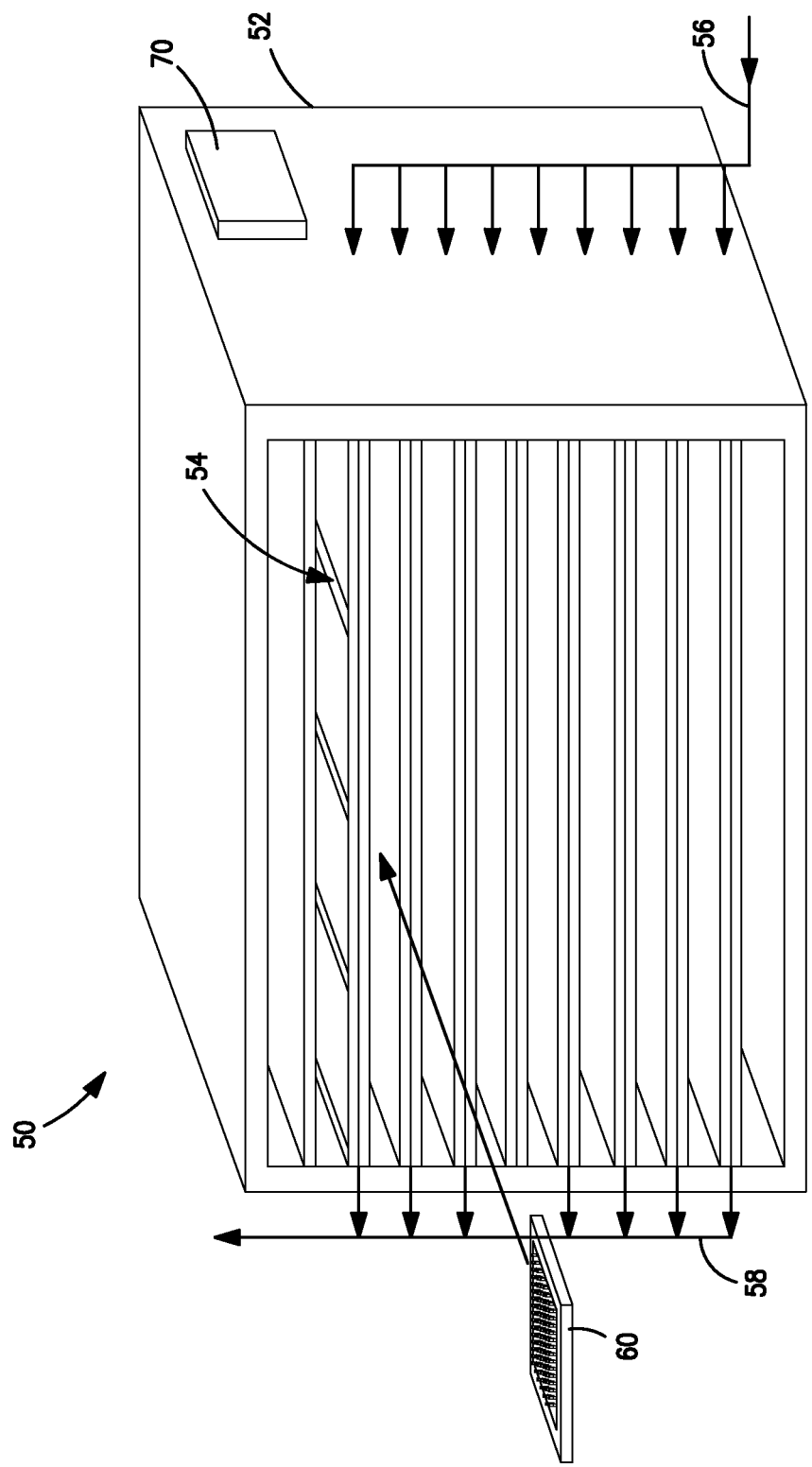
FIG. 4 is a schematic view of an embodiment of a multi-batch or large commercial scale uniform flow cooling chamber incorporating the features and advantages of the presently disclosed system and method.
Figure 5:
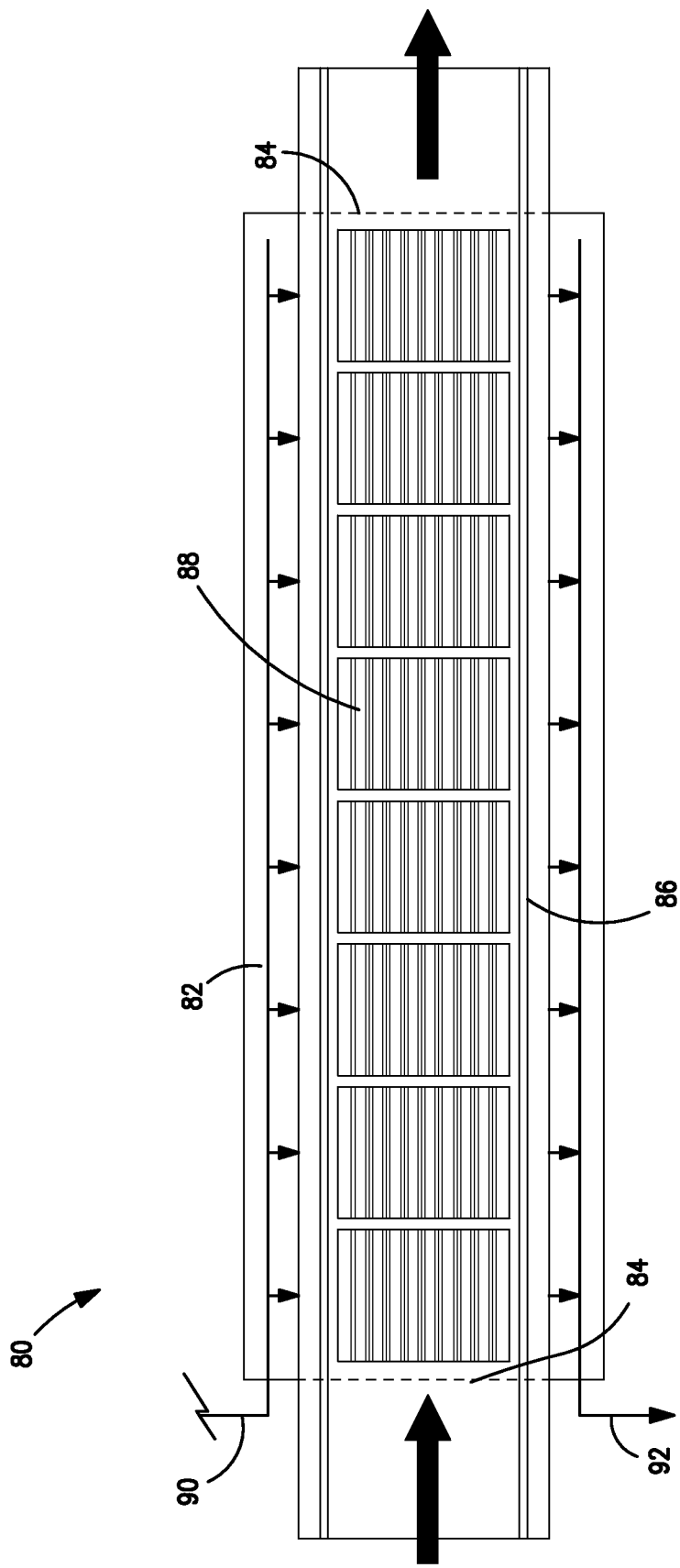
FIG. 5 is a schematic view of another embodiment of a continuous type uniform flow cooling unit incorporating the features and advantages of the presently disclosed system and method.

FIGS. 3, 4, and 5 depict various embodiments of the present controlled rate freezer or cryogenic chiller incorporating the uniform flow approach or concept. More specifically, FIG. 3 is a picture of a single modular unit 40 of the controlled rate freezer adapted to hold one of the uniform flow cryogenic chillers. The external housing for the unit 40 pictured in FIG. 3 is solid stainless steel housing with a gas injection box 44 having an intake conduit 42, a plenum, and porous plate 46 as well as a gas removal box 48 having a porous plate, an exhaust manifold, and an exhaust conduit. The pictured unit is dimensioned to hold a single laminar and uniform flow cryogenic chiller as described above with reference to FIGS. 1 and 2.

FIG. 4 depicts a multi batch or commercial scale unit 50 that includes a cooling chamber 52 that includes a plurality of shelves or rails 54 adapted to hold multiple uniform flow cryogenic chiller assemblies. Such multi-batch or commercial scale unit 50 is preferable capable of cryopreserving 50,000 or more vials or other such containers per production run. As seen in FIG. 4, the cryogen intake circuit 56 and spent gas exhaust circuit 58 are designed and sized to circulate sufficient cryogen to the multiple individual cryogenic chillers 60. Control system 70 is used to operatively control the temperature profile of the cold cryogen gas provided to each shelf 54, or to each cryogenic chiller assembly 60 depending on the inputs from the thermal sensors disposed within the system.

FIG. 5 depicts yet another possible commercial scale embodiment of the controlled rate freezer or chiller system 80 that operates in a continuous or conveyorized manner. Again, the unit 80 and cryogen cold gas intake circuit 90 and gas exhaust circuit 92 are designed and sized to circulate sufficient cryogenic cold gas to individualized containers or tray assemblies 88 disposed along a conveyor 86 within the tunnel-type freezer chamber 82 having an entrance and exit means 84. In this continuous operation, the cooling profiles of different containers, vials or trays could be either time based, as described above with regard to the batch systems, or spatially based (e.g. spatial location within the chamber).

The ability to precisely control the cooling rate of biological material provides many benefits. For example, biological material frozen in an aqueous solution may experience various stresses during the freezing and subsequent thawing process that may impair the function or activity of the material. Ice formation may physically disrupt the material or create severe changes in the interfacial bonding, osmotic forces, solute concentrations, etc. experienced by the material. Proper design of the freezing process can mitigate such stresses and the present system and method allows for the precise control of the freezing process to achieve uniformity in the frozen material in all vials accordance with the designed freezing profile.

Figure 9:
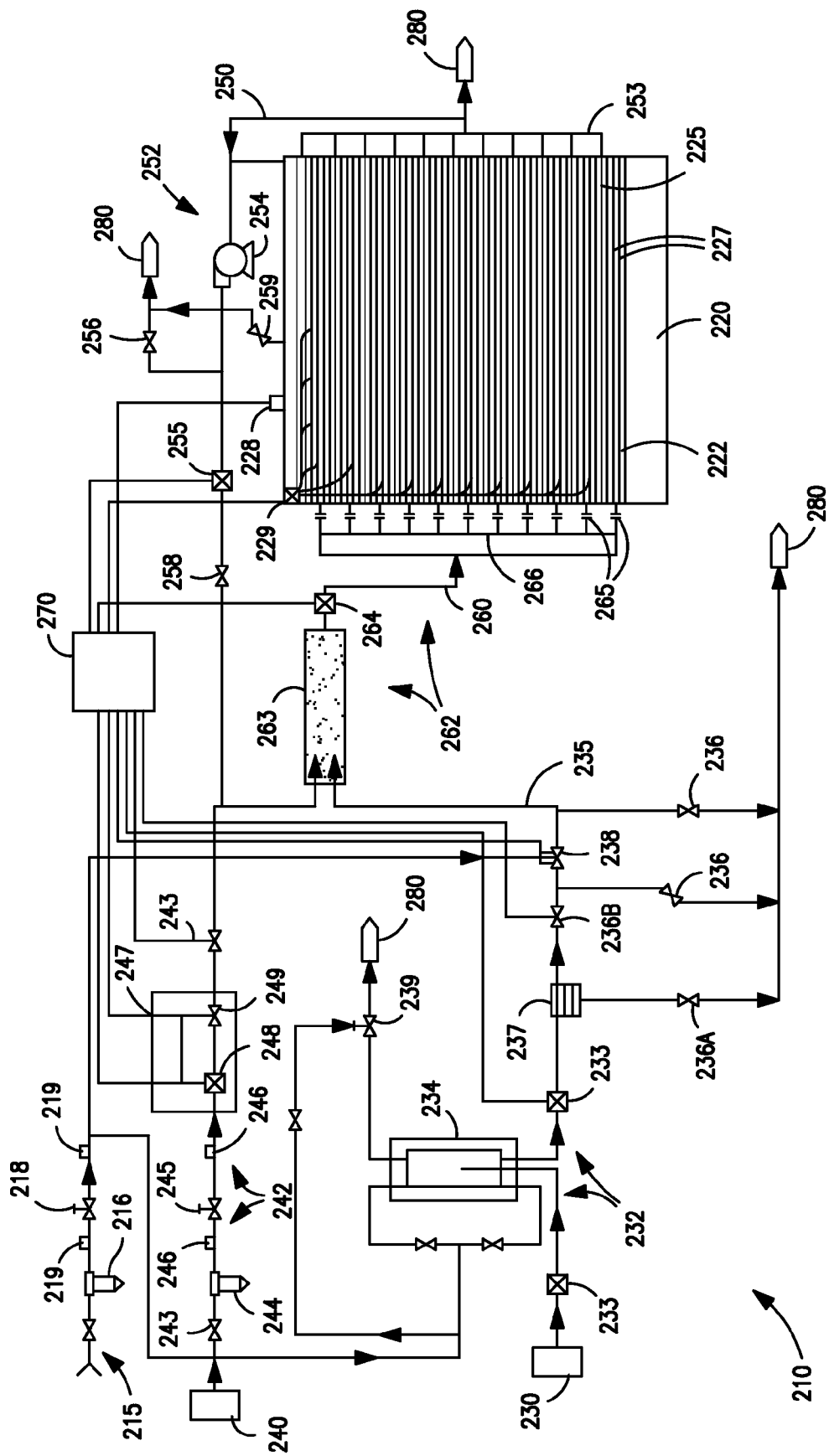
FIG. 9 depicts a multi-batch or commercial scale uniform flow cooling system with more detailed views of the process and instrumentation aspects of the gas intake, exhaust and recirculation circuits.

Turning not to FIG. 9, the illustrated cryogenic chiller system 210 includes a cooling chamber 220 adapted to receive a cryogenic cold gas 260 from a cryogen cold gas circuit 262, a source of liquid nitrogen 230, a liquid supply circuit 232 including a phase separator 234, a supply of gaseous nitrogen 240, a gas supply circuit 242, a recirculating cryogenic gas 250 and a gas recirculation circuit 252. The cryogenic chiller system 210 further includes a programmable logic controller (PLC) based control system 270 that operatively controls the fluid circuits in response to measured temperatures and pressures as well as certain user defined parameters including the desired cooling profiles.

The illustrated cooling chamber 220 has a plurality of cooling shelves 222 used to cool a large number of vials containing pharmaceutical active ingredients or active biological molecules. A cryogenic cold gas 260 is supplied to the cooling chamber 220 from a static in-line mixer 263 that mixes liquid nitrogen from the source of liquid nitrogen 230 via the liquid supply circuit 232 with a precisely metered gaseous nitrogen gas stream from the gas supply circuit 242 and recirculating cryogenic gas 250 from the gas recirculation circuit 252.

The temperature of the cryogenic cold gas 260 is preferably measured with a temperature sensor 264 disposed downstream of the static in-line mixer 263. By precisely adjusting the flow of nitrogen from the liquid supply circuit 232 with nitrogen gas from the gas supply circuit 242 and the gas recirculation circuit 252 it is possible to rapidly shift the temperature of the cryogenic cold gas 260 which allows cooling of the vials in the cooling chamber 220 with a wide range of cooling profiles to optimize operating conditions and maximize cell viability, drug uniformity, as well as drug potency.

Once a cryogenic cold gas 260 is formed by mixing this nitrogen gas with liquid nitrogen, it is split into multiple levels of cooling shelves 222 in a single cooling chamber 220. To provide the exact split of the cryogenic cold gas 260 to the multiple cooling shelves 222, a plurality of critical flow orifices 265 are used to split to cryogenic cold gas 260 into multiple gas streams. Under critical choke flow conditions, the cryogenic cold gas flow to the cooling shelves 222 is maintained independent of the downstream pressure. A large cryogenic cold gas manifold 266 is used to eliminate or minimize pressure differences upstream of the critical flow orifices 265 while the downstream gas flow resistance has no impact on the gas flow through the critical flow orifices 265. In this manner, the cryogenic cold gas flow to each of cooling shelves 222 in the cooling chamber 220 is nearly identical.

The cryogenic chiller system 210 is a direct contact cooling system with a cryogenic cold gas 260 flowing in the same direction with respect to each vial and preferably along the longitudinal axis of the vials, thus creating an extreme uniform cooling profile for all the vials. A porous metallic membrane (See FIGS. 1 and 2) provides uniform resistance across all the cooling surfaces, thus allowing the individual vials to receive identical or uniform amount of refrigeration.

The nitrogen gas supply 240 is preferably received from a bulk storage tank and is directed through a filter 244 to remove particulate materials. The nitrogen gas supply 240 is then regulated down to the desired pressure through a discharge pressure regulator 245. Line pressures before and after the pressure regulator 245 are preferably monitored using one or more pressure indicators 246. A mass flow controller 247 including a mass flow sensor 248 with electro-pneumatic control valve 249 is preferably used to control and maintain a precisely metered nitrogen gas flow rate through the gas supply circuit 242 to the static in-line mixer 263. An electrical solenoid valve 243 is also included in the gas supply circuit 242 to provide positive shut off capability when the cryogenic chiller system 210 is not operating. Alarms can be set in the control system 270 to deactivate this solenoid valve 243 if emergency shut down of the cryogenic chiller system 210 is required.

The illustrated system depicts an additional source of gas, namely air, to be used to operate various control valves. The illustrated air supply circuit 215 includes a filter 216 adapted to remove any particulates from the line, a pressure regulator 218 that is adapted to reduce the air pressure to about 25 psig for safe operation, and one or more pressure indicators 219 used to monitor the pressure in the air supply circuit 215.

The liquid nitrogen supply circuit 232 includes a source of liquid nitrogen 230, a phase separator 234, one or more temperature and pressure sensors 233, a liquid nitrogen manifold 235, one or more safety/relief valves 236, a strainer 237, and a primary cryogenic flow control valve 238. All liquid nitrogen piping is preferably insulated so as to minimize any phase change of the liquid nitrogen to nitrogen gas and the resulting two-phase flow in any of the pipes within the liquid nitrogen supply circuit 232.

The liquid nitrogen phase separator 234 is designed to remove any nitrogen gas that forms in the liquid nitrogen supply circuit 232 due to heat leak or changes in pipeline pressures. The illustrated phase separator 234 is a double-walled, vertically mounted, cylindrical tank. The inner liquid vessel has a maximum allowable working pressure (MAWP) rating of 250 psig, with the outer vessel providing a vacuum insulation. The gas phase vent valve 239 operatively controls the filling of the phase separator 234 with liquid nitrogen from the source of liquid nitrogen 230. At a low liquid level, the gas phase vent valve 239 opens to vent 280 vapor pressure from the phase separator 234, allowing liquid nitrogen to transfer from the source of liquid nitrogen 230. As the liquid nitrogen level increases in the phase separator 234, gas phase vent valve 239 begins to close and the fill rate decreases until the valve 239 is completely closed and filling of the phase separator 234 with liquid nitrogen stops.

The strainer 237 is coupled to a blow-down relief valve 236A that is operated as required to clean the strainer 237 or purge any vaporized nitrogen gases from the liquid nitrogen supply circuit 232. The strainer 237 also serves to filter out any particulates in the liquid nitrogen so as to avoid adverse performance or damage to the primary cryogenic control valve or relief valves.

One of the illustrated safety valves is a cryogenic electrical solenoid valve 236B that provides positive shutoff of the liquid nitrogen supply. Deactivating the electrical solenoid valve 236B shuts off all liquid nitrogen flow through the liquid nitrogen supply circuit and to the static in-line mixer 263. This electrical solenoid valve 236B is configured such that cutting electrical power immediately stops the liquid nitrogen flow through the liquid nitrogen supply circuit 232 circuit and vent 280 any trapped liquid nitrogen from the circuit. In addition, other process shutdown and the emergency shutoff procedures within the control system 270 generate command signals to the one or more safety valves 236. For example, when the cryogenic chiller system 210 has stopped operating at the end of the freezing cycle or for other reasons including preset alarm conditions. The control system 270 stops the liquid nitrogen flow in the liquid nitrogen supply circuit 232 by shutting off one or more of the safety valves 236.

The primary cryogenic flow control valve 238 receive signals from the control system 270 to control the amount of liquid nitrogen supplied to the cryogenic cold gas circuit 262 in response to measured temperatures and pressures within the cryogenic chilling system 210 as well as certain user defined parameters including the desired cooling profiles.

Liquid nitrogen from the liquid nitrogen supply circuit 232 is directed to the static in-line mixer 263. The liquid nitrogen evaporates into a cryogenic cold gas 260 by mixing with the nitrogen gas directed from the gas supply circuit 242 and the gas recirculation circuit 252. The static in-line mixer 263 is used to ensure that no slug of unevaporated liquid nitrogen enters the cooling chamber 220. The temperature in the cryogenic cold gas circuit 262 is monitored with a temperature sensor 264 disposed at or near the exit of the static in-line mixer 263. The control system 270 receives this measured temperature and regulates the liquid nitrogen flow rate and gas flow rates to the static in-line mixer 263 in response thereto based on programmed temperature profiles and preset parameters.

Downstream of the static in-line mixer 263, the cryogenic cold gas 260 is directed to a large cryogenic cold gas manifold 266 and then to the multiple cooling shelves 222 in the cooling chamber 220 via a plurality of critical flow orifices 265. The large cryogenic cold gas manifold 266 is used to ensure that all the gas distribution points realize the same or similar pressures. The actual cryogenic cold gas flow rate delivered to each of the cooling shelves 222 of the cooling chamber 220 is determined by the size of the critical flow orifice 265 associated with each cooling shelve 222.

Inside the cooling chamber 220 at each level, there are a series of gas distribution pipes with downward oriented nozzles. The purpose of the additional gas distribution pipes inside the cooling chamber is to avoid or minimize velocity generated local pressure gradients that may impact the cryogenic cold gas distribution across any large porous metallic membrane. With the critical flow orifices 265 and gas distribution networks, a large cooling chamber can be used holding thousands of vials or packages with very high degree of cooling uniformity.

The cooling surfaces within the multiple levels of the cooling chamber 220 are made of porous metallic membranes 227 adapted to generate uniform gas flow across the plurality of vials. Due to the small pore size and high flux in the metallic membranes 227, a laminar flow rising from the entire cooling surface is generated. While a laminar flow from the cooling surface is preferred, a turbulent gas flow is tolerable so long as the flow remains parallel to the vials and that macro recirculation of the gas does not occur inside the cooling chamber 220.

Above the porous metallic membranes at each level in the cooling chamber 220 is an exhaust manifold 225 with a perforated plate disposed in a parallel orientation with the porous metallic membranes 227 to maintain the uniform flow of the cryogenic cold gas 260 during the cooling of the vials. The gas received in the exhaust manifold 225 is immediately removed from the cooling chamber 220 in order to avoid or minimize any internally recirculating flow of the spent nitrogen gas. It is important to avoid the internal recirculation of the nitrogen gas as such recirculated gas is generally at a warmer temperature than the cryogenic cold gas 260 supplied to the cooling chamber 220. Such internally recirculating flow is the main cause of temperature non-uniformity with edge effects in prior art or conventional laminar cooling devices.

The exhausted gas removed from the cooling chamber 220 is preferably diverted to a gas recirculation circuit 252. The illustrated gas recirculation circuit 252 includes a recirculating gas manifold 253 disposed between the exhaust manifolds 225 in the cooling chamber 220 and a recirculating blower 254 that starts automatically during the later part of the freezing cycle. The gas recirculation circuit 252 also includes a mass flow meter 255 coupled to the control system 270 that measures the flow through the gas recirculation circuit 252 so as to adjust the make up gas flow rate from the gas supply circuit 242 to maintain a desired level of cryogenic cold gas 260 flow in the cryogenic cold gas circuit 262. Back pressure regulator 256 maintains the pressure from the recirculating blower 254 while check valve 258 keeps the make up nitrogen gas from the gas supply circuit 242 from entering the gas recirculation circuit 252 when the recirculation blower 254 is not operating. Safety relief valve 259 provides over-pressurization protection for the cooling chamber 220 in case there are blockages in the gas recirculation circuit 252.

The pressure and temperature inside the cooling chamber 220 are monitored with pressure gauge 228 and temperature sensors 229 or thermocouples disposed within the cooling chamber 220 proximate some of the vials. The pressure gauges 228, temperature sensors 229 sensors as well as the thermocouples are coupled to and provide inputs to the control system 270.

The disclosed systems and methods are particularly well-suited for commercial type or large scale biological production operations since the process is conducted using the same equipment and process parameters that are easily scaled or adapted to manufacture a wide range of biological products. The presently disclosed process provides for the controlled rate freezing of biological materials using a process that achieves a high degree of uniformity in cooling or freezing of the biological material from sample to sample, vial to vial, container to container, and batch to batch.

In addition, a closer examination of FIGS. 5-8 illustrates that the present freezing or chilling process can be used as a means to initiate and control the nucleation of freezing in biological materials. As illustrated in FIGS. 5 through 8, the nucleation of freezing of the biological materials in all vials monitored occurred at roughly the same time and same temperature. Nucleation of freezing is exhibited by the concurrent short spike in sample temperature (see 100, 110, 120) as a result of the exothermic process occurring during the phase change occurring in the samples. Thus, nucleation control is possible by precisely controlling the timing and magnitude of the sharp or rapid temperature quench using the above described controlled freezing systems and methods. When compared to the wide spectrum of times and temperatures in the nucleation of freezing that results from use of conventional controlled rate freezers, the present system and method provides a greater degree of control which likely impacts other performance aspects and characteristics of the preserved biological material. Also, as the contemplated nucleation initiation and control is temperature driven, it works equally well in open or closed containers or vials.

Preferably, the housings for the units in FIGS. 3, 4, 5 and 9 are pressure rated housings such that the present controlled rate freezing method can be combined with or can incorporate aspects of the controlled nucleation system and process, as generally described in U.S. patent application Ser. No. 11/702,472 the disclosure of which is incorporated by reference herein.

From the foregoing, it should be appreciated that the present invention thus provides a system and method of controlled rate freezing of biological materials. Various modifications, changes, and variations of the present methods will be apparent to a person skilled in the art and it is to be understood that such modifications, changes, and variations are to be included within the purview of this application and the spirit and scope of the claims.

What is claimed is:

1. A controlled rate cryogenic chiller or freezing system for biological solutions or biopharmaceutical materials contained in a plurality of vials or containers, comprising:
    a cryogen source;
    an intake circuit coupled to the cryogen source and adapted for providing a uniform flow of a cryogen cold gas to a cooling chamber;
    the cooling chamber comprising an intake plenum having a base gas injection box and a first porous plate or perforated plate disposed on a surface of the gas injection box, an exhaust manifold having a gas removal box of similar size to the base gas injection box and disposed proximate to the base gas injection box and a second porous plate or perforated plate disposed therein, the second porous plate or perforated plate being parallel and opposing to the first porous plate or perforated plate, and wherein the first and second parallel and opposing porous plates or perforated plates are of similar size and configuration and define a cooling area therebetween;
    an exhaust circuit adapted to remove the cryogen gas from the exhaust manifold of the cooling chamber; and
    a control system that adjusts the flow rates of the cryogen source in the intake circuit and any cryogen gas in the exhaust circuit to adjust the temperature of the cold cryogen gas delivered to the cooling chamber in response to a desired cooling rate of the biological solutions or biopharmaceutical materials and measured temperatures within the cooling chamber;
    wherein the biological solutions or biopharmaceutical materials contained in the plurality of vials or containers are spaced apart on at least one of the parallel and opposing porous plates or perforated plates; and
    wherein a uniform, uni-directional flow of temperature adjusted cryogenic cold gas is delivered to the cooling area between the parallel and opposing porous plates or perforated plates and along a longitudinal axis of each of the plurality of vials or containers to cool the biological solutions or biopharmaceutical materials at a uniform cooling rate and prevent recirculation of the cryogenic cold gas within the cooling area.

2. The system of claim 1 wherein the cryogen source further comprises a liquid cryogen and a warmer gas.

3. The system of claim 2 wherein the intake circuit further comprises an in-line mixer adapted to mix the liquid cryogen and warmer gas to produce the cryogenic cold gas.

4. The system of claim 3 wherein the exhaust circuit further comprises a recirculation circuit that recirculates gas from the exhaust manifold back to the intake circuit.

5. The system of claim 4 wherein the control system operatively adjusts the flow rates of the liquid cryogen, the warmer gas in the intake circuit and recirculation circuit to adjust the temperature of the cold cryogen gas delivered to the cooling chamber.

6. The system of claim 1 wherein the intake circuit further comprises one or more critical flow orifices disposed upstream of the intake plenum to choke the flow of cryogenic cold gas to the cooling chamber.

7. A method of controlled rate freezing or chilling of biological solutions or biopharmaceutical materials comprising the steps of:
    placing a plurality of vials or containers of the biological solutions or biopharmaceutical materials in a cooling area defined as the area between opposing parallel porous plates or perforated surfaces within a cooling chamber;
    mixing a liquid cryogen with a warmer gas to produce a cold cryogenic gas at a selected temperature profile, the temperature profile corresponding to a desired cooling rate of the biological solutions or biopharmaceutical materials within the vials or containers; and
    delivering a uniform and uni-directional flow of the temperature adjusted cryogenic cold gas through one of the opposing parallel porous plates or perforated surfaces to the cooling area and along a longitudinal axis of each of the plurality of vials or containers disposed in the cooling area to cool the biological solutions or biopharmaceutical materials at a uniform cooling rate, and
    promptly exhausting the gas from the cooling area and cooling chamber via the other opposing parallel porous plate or perforated surface so as to prevent recirculation of the gas within the cooling area.

8. The method of claim 7 further comprising the step of recirculating the exhausted gas to mix with the warmer gas.

9. The method of claim 7 further comprising the step of regulating the pressure and flow rate of the temperature adjusted cryogenic cold gas prior to delivering the uni-directional, laminar flow through the to the cooling area.

10. A controlled rate cryogenic chiller or freezing system for biological solutions or biopharmaceutical materials contained in a plurality of vials or containers comprising:
    a cryogen source;
    an intake circuit coupled to the cryogen source and adapted for providing a uniform flow of a cryogen cold gas to a cooling chamber;
    the cooling chamber comprising an intake plenum, an exhaust manifold, and two or more parallel porous surfaces that define a cooling area between adjacent parallel surfaces with one of the parallel porous surfaces disposed adjacent to the intake plenum and in fluid communication with the intake plenum and another of the parallel porous surfaces disposed adjacent to the exhaust manifold, the parallel porous surfaces and cooling area adapted to retain a plurality of containers of biological materials;

an exhaust circuit adapted to remove the cryogen gas from the exhaust manifold of the cooling chamber; and a control system adapted adjust the flow rates of the cryogen source in the intake circuit and any cryogen gas in the exhaust circuit to adjust the temperature of the cold cryogen gas delivered to the cooling chamber in response to a desired cooling rate of the biological materials and measured temperatures within the cooling chamber;

wherein a uniform, uni-directional and laminar flow of temperature adjusted cryogenic cold gas is delivered to the cooling area along a longitudinal axis of the plurality of vials or containers to uniformly cool the biological solutions or biopharmaceutical materials and prevent recirculation of the cryogenic cold gas within the cooling area.

* * * * *